(12) United States Patent
Yamashita et al.

(10) Patent No.: US 6,372,941 B1
(45) Date of Patent: Apr. 16, 2002

(54) PROCESSES FOR PRODUCING β-HALOGENO-α-AMINO-CARBOXYLIC ACIDS AND PHENYLCYSTEINE DERIVATIVES AND INTERMEDIATES THEREOF

(75) Inventors: Koki Yamashita, Kobe; Kenji Inoue, Kakogawa; Koichi Kinoshita, Takasago; Yasuyoshi Ueda, Himeji; Hiroshi Murao, Takasago, all of (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 09/582,461

(22) PCT Filed: Dec. 28, 1998

(86) PCT No.: PCT/JP98/05983

§ 371 Date: Aug. 14, 2000

§ 102(e) Date: Aug. 14, 2000

(87) PCT Pub. No.: WO99/33785

PCT Pub. Date: Jul. 8, 1999

(30) Foreign Application Priority Data

Dec. 27, 1997 (JP) .............................. 9-367814
Jul. 1, 1998 (JP) ........................... 10-186314
Sep. 18, 1998 (JP) ........................... 10-264397

(51) Int. Cl.$^7$ ................. C07C 229/00; C07C 205/00; C07C 207/00
(52) U.S. Cl. ................. 562/574; 562/553; 562/444; 562/445
(58) Field of Search ................. 562/574, 553, 562/444, 445

(56) References Cited

U.S. PATENT DOCUMENTS 4,985,522 A * 1/1991 Mathias et al.

FOREIGN PATENT DOCUMENTS

| EP | 0 754 759 A1 | 1/1997 |
| JP | 60-258158 | 12/1985 |

OTHER PUBLICATIONS

Portelli (1989). On the synthesis of B–phenylalanine. Gazzetta Chimica Italiana 119(4), pp 215–216.*

* cited by examiner

Primary Examiner—Gary Geist
Assistant Examiner—Mahreen Chaudhry
(74) Attorney, Agent, or Firm—Connolly Bove Lodge & Hutz LLP.

(57) ABSTRACT

An industrially advantageous method of producing β-halogeno-α-aminocarboxylic acids is provided. Methods are also provided of producing optically active N-protected-S-phenylcysteines having high optical purity and of intermediates thereof, respectively, in which the above production method is utilized.

A method of producing β-halogeno-α-aminocarboxylic acids or salts thereof is disclosed which comprises halogenating the hydroxyl group of a β-hydroxy-α-aminocarboxylic acid (in which the basicity of the amino group in α-position is not masked by the presence of a substituent on said amino group) or a salt thereof with an acid with a halogenating agent. A method of producing optically active N-protected-S-phenylcysteines represented by the general formula (3) or salts thereof is further disclosed which comprises applying the above production method to optically active serine or a salt thereof and then carrying out treatment with an amino-protecting agent and reaction with thiophenol under a basic condition.

(3)

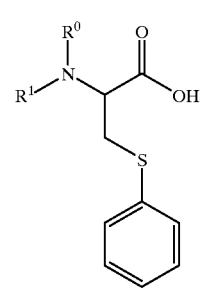

28 Claims, No Drawings

US 6,372,941 B1

PROCESSES FOR PRODUCING β-HALOGENO-α-AMINO-CARBOXYLIC ACIDS AND PHENYLCYSTEINE DERIVATIVES AND INTERMEDIATES THEREOF

TECHNICAL FIELD

The present invention relates to a method of producing a β-halogeno-α-aminocarboxylic acid or a salt thereof, which is useful as a raw material for the production of medicinals, among others. The invention also relates to a method of producing an optically active N-protected S-phenyl-L-cysteine or a salt thereof, which is useful as an intermediate of medicinals, in particular anti-AIDS drugs, and to a method of producing an intermediate thereof.

BACKGROUND ART

The following methods, among others, are known for producing β-halogeno-α-aminocarboxylic acids:

(1) The method which comprises derivatizing a β-hydroxy-α-aminocarboxylic acid into the corresponding β-hydroxy-α-aminocarboxylic acid ester, then halogenating the hydroxyl group thereof with a phosphorus halide to give the corresponding β-halogeno-α-aminocarboxylic acid ester, and hydrolyzing the ester group using a hydrohalogenic acid to give the objective β-halogeno-α-aminocarboxylic acid. Specifically, serine is derivatized into serine methyl ester hydrochloride, the ester salt is then treated with phosphorus pentachloride to give α-amino-β-chloropropionic acid methyl ester hydrochloride, which is further hydrolyzed with hydrochloric acid. The resulting α-amino-β-chloropropionic acid hydrochloride is isolated by concentrating the reaction mixture to dryness, followed by crystallization of the residue from a mixture of 1-propanol and hydrochloric acid [e.g. CHIRALITY, 8:197–200 (1996)]; and (2) The method which comprises treating β-phenylserine monohydrate with thionyl chloride and then with concentrated hydrochloric acid to give β-chloro-β-phenylalanine [Gazzetta Chimica Italiana, 119 (1989) p. 215].

However, in the above method (1), the halogenation of the hydroxyl group in β position usually involves three reaction steps, namely protection of the carboxyl group, halogenation of the hydroxyl group in β position and deprotection of the carboxyl group. In this case, many difficulties are encountered, for example the multiplicity of steps required, procedural complexity and low yields.

In the above method (2), such difficulties arise as the use of thionyl chloride in large amounts for the same to serve also as a solvent and the resulting complicatedness of procedure. As a result of investigations made by the present inventors, it was further found that the method is hardly applicable to the chlorination of serine, threonine or the like.

Thus, no efficient technology has been established for producing β-halogeno-α-aminocarboxylic acids on a commercial scale.

On the other hand, such methods of producing optically active S-phenylcysteine derivatives as mentioned below are known in the art:

<Derivatization from Serine>

1) The method comprising reacting serine with thiophenol in the presence of tryptophan synthase (EP 754759);
2) The method which involves lactonization of a serine derivative with an azodicarboxylic acid ester [J. Am. Chem. Soc., 1985, vol. 107, p. 7105; Synth. Commun., 1995, vol. 25 (16), p. 2475];
3) The method comprising converting the hydroxyl group of an N-protected serine ester derivative to a sulfonyloxy group and substituting a thiophenyl group therefor [Tetrahedron Lett., 1987, vol. 28, p. 6069; ibid., 1993, vol. 34, p. 6607; EP 604185 A1];

<Derivatization from Starting Compounds other than Serine>

4) The method comprising reacting cysteine with a phenyldiazonium salt in the presence of a copper salt [J. Org. Chem., 1958, vol. 23, p. 1251];
5) The method comprising derivatizing from an aziridinecarboxylic acid derivative in the presence of boron trifluoride-ethyl ether complex [Bull. Chem. Soc. Jpn, 1983, vol. 56, p. 520];
6) The method comprising reacting cysteine with iodobenzene in the presence of a copper salt [Aust. J. Chem., 1985, vol. 38, p. 899]; and
7) The method comprising reacting dehydroalanine with a chiral nickel complex [Tetrahedron, 1988, vol. 44, p. 5507].

Since optically active serine, in particular L-serine, is a readily available compound, a practical method would be provided if the starting material L-serine could be converted efficiently to an optically active S-phenylcysteine derivative. However, the method 1), in which a particular enzyme is utilized, and the method 2), in which a lactone derivative is used as an intermediate, have problems from the viewpoint of operability, productivity, safety in reagents handling, and economy, among others. The method 3), in which the hydroxyl group of an N-protected serine ester derivative is converted to a sulfonyloxy group and the resulting product is then subjected to substitution reaction using the sodium salt of a thiol in N,N-dimethylformamide, is also disadvantageous in that because it involves the use of a reagent relatively difficult to handle, for example sodium hydride or potassium hydride, as a base, it does not always give the desired N-protected S-phenylcysteine ester in high yield and, in particular, the optical purity is decreased, as revealed by a study made by the present inventors.

On the other hand, the methods 4) through 7), which comprise derivatization from other starting compounds than serine, cannot be said to be industrially advantageous, either, since, for example, the waste treatment is troublesome, materials requiring caution in handling or expensive materials are used and the yield and productivity are low.

In view of the above state of the art, the primary object of the present invention is to provide a method of producing β-halogeno-α-aminocarboxylic acids in an industrially advantageous manner and a method of producing optically active S-phenylcysteine derivatives from optically active serine, which is readily available commercially, in an industrially advantageous manner.

SUMMARY OF THE INVENTION

As a result of their intensive investigations made in an attempt to develop an industrially advantageous method of producing β-halogeno-α-aminocarboxylic acids, the present inventors have surprisingly found an industrially advantageous production method according to which β-halogeno-α-aminocarboxylic acids can be synthesized in an efficient manner by treating aβ-hydroxy-α-aminocarboxylic acid or a salt thereof with an acid with a halogenating agent.

On the other hand, in efficiently producing optically active S-phenylcysteine derivatives from optically active serine, namely L- or D-serine, the point is how to prevent the optical purity from decreasing in thiophenylating the activated compound derived from optically active serine by converting its hydroxyl group to a leaving group. The present inventors thought that there would be the possibility of attaining the above object in an industrially advantageous manner while preventing racemization if an adequately activated carboxylic acid derivative could be synthesized from optically active serine by activating the hydroxyl group thereof in the form of a leaving group and if the thiophenylation could be realized efficiently. Based on this way of thinking, they made intensive investigations and, as a result, found that optically active β-chloroalanine can be synthesized in an efficient manner when the above method of producing β-halogeno-α-aminocarboxylic acids is utilized. There are no prior art findings teaching or suggesting that optically active β-chloroalanine can be produced by directly chlorinating optically active serine or a salt thereof. The relevant method of production is thus novel.

In addition, it was found that the optically active β-chloroalanine obtained in the above manner can be converted to an optically active N-protected-β-chloroalanine by treatment with an amino-protecting agent and that said compound can be converted to an optically active N-protected-S-phenylcysteine by reacting with thiophenol under a basic condition. Based on these and other findings, the present invention has now been completed. Particularly when the above three-step process is used, optically active N-protected-S-phenylcysteine derivatives can be produced in an industrially advantageous manner without any substantial reduction in the optical purity of the starting material, namely optically active L- or D-serine.

Thus, the present invention relates to a method of producing a β-halogeno-α-aminocarboxylic acid or a salt thereof which comprises halogenating the hydroxyl group of a β-hydroxy-α-aminocarboxylic acid (in which the basicity of the amino group in a-position is not masked by the presence of a substituent on said amino group) or a salt thereof with an acid by treating the same with a halogenating agent.

The present invention also relates to a method of producing an optically active N-protected-β-chloroalanine of the general formula (2) or a salt thereof according to the above method of production:

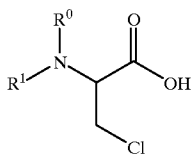

(2)

wherein $R^1$ represents an amino-protecting group and $R^0$ represents a hydrogen atom or, taken together with $R^1$, an amino-protecting group, namely by preparing an optically active β-chloroalanine of the formula (1) or a salt thereof:

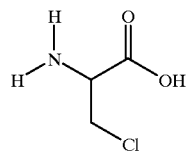

(1)

from an optically active serine or a salt thereof with an acid, and then treating the same with an amino-protecting agent.

The present invention further provides a method of producing an optically active N-protected-S-phenylcysteine of the general formula (3) or a salt thereof:

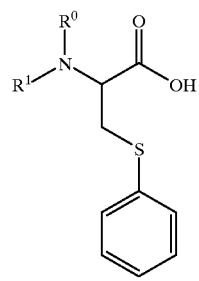

(3)

wherein $R^1$ represents an amino-protecting group and $R^0$ represents a hydrogen atom or, taken together with $R^1$, an amino-protecting group, which comprises preparing an optically active N-protected-β-chloroalanine or a salt thereof according to the production method mentioned above and then reacting the same with thiophenol under a basic condition.

In the following, the invention is described in detail.

DETAILED DISCLOSURE OF THE INVENTION

The β-hydroxy-α-aminocarboxylic acid to be used in the practice of the invention is not particularly restricted but, basically, is one whose amino group retains its basicity without being masked by the presence of a substituent thereon, for example an acyl type amino-protecting group. The basic skeleton of the above β-hydroxy-α-aminocarboxylic acid is α-amino-β-hydroxypropionic acid (also called serine), and one, two or three of the three hydrogen atoms on the carbon chain other than those of the amino, hydroxyl and carboxyl groups of the basic skeleton may be substituted with another group or other groups unless the halogenation reaction is adversely affected. Further, one or two of the hydrogen atoms of the above amino group may be substituted with a substituent or substituents (e.g. alkyl, aralkyl, aryl, etc.) unless the halogenation reaction is adversely affected and unless the basicity of the amino group is jeopardized.

As typical examples of the β-hydroxy-α-aminocarboxylic acid, there may be mentioned, among others, serine, threonine, allothreonine, β-phenylserine and the like. The salt of the β-hydroxy-α-aminocarboxylic acid with an acid is not particularly restricted, either, but includes, among others, such salts as serine hydrochloride, threonine hydrochloride, allothreonine hydrochloride and β-phenylserine hydrochloride. The above salt may be prepared and isolated in advance, or may be prepared in the reaction vessel or formed during reaction. When these β-hydroxy-α-aminocarboxylic acids are used, the products are β-halogeno-α-aminopropionic acids (i.e. β-haloalanines), β-halogeno- α-aminobutyric acids, β-halogeno-β-phenyl-α-aminopropionic acids (i.e. β-halophenylalanines), etc. It is a matter of course that the above β-hydroxy-α-aminocarboxylic acids may be used in an optically active form.

The halogenating agent to be used in the practice of the invention includes, among others, thionyl halides and phosphorus halides, specifically thionyl chloride, thionyl bromide, phosphorus pentachloride, phosphorus trichloride, phosphorus oxychloride, phosphorus tribromide, etc. From the viewpoint of reaction yield and ease of handling, however, thionyl halides are preferred, in particular thionyl chloride is most preferred. The above halogenating agent is used in an amount of, for example 1 to 10 moles, preferably 1 to 4 moles, more preferably 1 to 2 moles, per mole of the substrate β-hydroxy-α-aminocarboxylic acid or a salt thereof with an acid. Basically, the above amount is the number of moles of the basic skeletal unit of the βhydroxy-α-aminocarboxylic acid and, in cases where a plurality of such basic skeletal units as mentioned above are contained in each molecule or where the another or other substituents consume the halogenating agent or a group consuming said agent is contained, for instance, it is considered necessary to increase the amount of the halogenation agent by the corresponding equivalent amount.

The treatment with the halogenating agent in the production method of the present invention is preferably carried out in a solvent. Preferred as the solvent in that case are, for example, 1,2-dimethoxyethane, 1,4-dioxane, tetrahydrofuran, diethylene glycol dimethyl ether, triethylene glycol dimethyl ether, tetraethylene glycol dimethyl ether, polyethylene glycol dimethyl ether, tert-butyl methyl ether, dibutyl ether, diethyl ether and like ether solvents; acetonitrile, methylene chloride, ethyl acetate and other aprotic solvents. These maybe used singly or two or more of them may be used combinedly. Among them, ether solvents are preferred and, in particular, ether solvents miscible with water, such as 1,2-dimethoxyethane, 1,4-dioxane, tetrahydrofuran, diethylene glycol dimethyl ether, triethylene glycol dimethyl ether, tetraethylene glycol dimethyl ether and polyethylene glycol dimethyl ether, are more preferred. It is of course possible to use another solvent or other solvents within limits within which no adverse effect is produced.

The treatment with the above halogenating agent can be carried out in the presence of an amine or a salt thereof. The amine or the salt thereof is not particularly restricted but includes, for example, triethylamine, trimethylamine, diisopropylethylamine, tetramethylethylenediamine, pyridine, dimethylaminopyridine, imidazole, triethylamine hydrochloride, trimethylamine hydrochloride, diisopropylethylamine hydrochloride and the like. Among them, tertiary amines such as trimethylamine and triethylamine or salts thereof are preferred. More preferred is triethylamine or its hydrochloride.

The above amine or its salt is added preferably in an amount of 0.1 to 30 mole percent, more preferably 1 to 10 mole percent, based on the substrate β-hydroxy-α-aminocarboxylic acid or a salt thereof.

In a mode of practice of the present invention which is more preferred in attempting to attain a higher reaction yield, the treatment with the above halogenating agent, preferably thionyl chloride, is carried out in the presence of a hydrogen halide, preferably hydrogen chloride (gas). The hydrogen halide is used in an amount of, for example, not less than about 1 molar equivalent, preferably an amount exceeding 2.0 molar equivalents, more preferably an amount of not less than about 3 molar equivalents, based on the β-hydroxy-α-aminocarboxylic acid. Generally, by using the hydrogen halide in an amount of about 3 to 10 molar equivalents, it is possible to carry out the above treatment very smoothly. Like the case mentioned above, it is fundamentally understood that the amount mentioned above corresponds to the number of molar equivalents per basic skeletal unit of the β-hydroxy-α-aminocarboxylic acid (the hydrohalogenic acid salt of a β-hydroxy-α-aminocarboxylic acid corresponds to the presence of 1.0 molar equivalent of the corresponding hydrogen halide relative to the β-hydroxy-α-aminocarboxylic acid). The concentration of the hydrogen halide in the reaction mixture is, for example, not less than about 1 mole, preferably not less than about 2 moles, more preferably not less than about 3 moles, per liter of solvent. The above treatment can be carried out smoothly at a hydrogen halide concentration not higher than the saturated concentration in the reaction system. The above treatment may be carried out in the presence of an amine or a salt thereof.

Referring specifically to a simple reaction procedure taken as an example, a suspension composed of a β-hydroxy-α-aminocarboxylic acid (e.g. L-serine) and 1,4-dioxane, for instance, is almost or completely saturated with hydrogen chloride gas, thionyl chloride is then added and, after completion of the addition, the mixture is moderaly or vigorously stirred preferably at room temperature to 100° C., more preferably at 40 to 80° C., preferably for 0.5 to 30 hours, more preferably for 1 to 20 hours, to give the corresponding β-chloro-α-aminocarboxylic acid [e.g. L-α-amino-β-chloropropionic acid (also called β-chloro-L-alanine)].

The β-halogeno-α-aminocarboxylic acid obtained by the above halogenation may be isolated prior to the use in the next step or may be used without isolation.

The above β-halogeno-α-aminocarboxylic acid may be isolated, for example, by such a technique as column chromatography commonly used in isolating amino acids. Said acid can be isolated in a simple and efficient manner by the method mentioned below, however.

For isolating the above β-halogeno-α-aminocarboxylic acid in the form of a hydrohalogenic acid salt, for example hydrochloride, after completion of the reaction, during which the precipitation of the desired product proceeds (namely reaction/crystallization proceeds) with the progress of the treatment with the above halogenating agent, the reaction mixture is subjected, either as such or after concentration, to conventional treatment for solid-liquid separation, such as filtration or centrifugation, whereby the desired product can be recovered in a very simple manner and in high yields. In the step of isolation, it is of course possible to reduce the content of or remove those relatively low boiling components remaining in the reaction mixture after the halogenation reaction, such as sulfur dioxide, the excess hydrogen halide (e.g. hydrogen chloride) and the unreacted halogenating agent (e.g. thionyl halide), in advance, according to need. By concentrating the reaction mixture, it is also possible to recover the reaction solvent.

For isolating the above β-halogeno-α-aminocarboxylic acid in the free form, the acid coexisting in the reaction mixture after the halogenation reaction is converted to a salt, preferably a salt soluble in an organic solvent and water (e.g. lithium halide such as lithium chloride) using a base, preferably a basic lithium compound such as lithium hydroxide or lithium carbonate, for instance, and the above β-halogeno-α-aminocarboxylic acid is caused to crystallize out from an organic solvent, water or a medium composed of an organic solvent and water while causing dissolution of the above resulting salt in such medium. The subsequent separation using a conventional solid-liquid separation procedure, such as filtration or centrifugation, gives the desired product in a simple and convenient manner. Since, generally, the conversion of acids to salts is preferably carried out in the presence of water, it is desirable to attempt to reduce the solubility of the β-halogeno-α-aminocarboxylic acid, which is a water-soluble compound, or, in other words, increase the precipitate amount, by using a water-miscible organic solvent as said organic solvent.

The above water-miscible organic solvent specifically includes, but is not limited to, 1,2-dimethoxyethane, 1,4-dioxane, tetrahydrofuran, diethylene glycol dimethyl ether, triethylene glycol dimethyl ether, tetraethylene glycol dimethyl ether, polyethylene glycol dimethyl ether, acetonitrile, methanol, ethanol, n-propanol, isopropanol, tert-butanol and acetone, among others. Among these, acetone, in particular, is preferred from the viewpoint of increased precipitation of water-soluble β-halogeno-α-aminocarboxylic acids, production of crystals having good characteristics, ease of handling and inexpensiveness, among others.

Since the above β-halogeno-α-aminocarboxylic acid has a high solubility in water, it is desirable, for attaining increased precipitation, to reduce the amount of water, use the above water-miscible organic solvent in a volume ratio of not less than 1 relative to water and maintain the final cooling temperature at a low level, preferably not higher than 10° C., more preferably not higher than 0° C. The solubility of the above β-halogeno-α-aminocarboxylic acid tends to increase in the presence of lithium chloride or the like, hence it is effective to use acetone combinedly so that the precipitation may be maximized.

In the step of adding a basic lithium compound for converting the coexisting acid to the salt form for causing precipitation of the above β-halogeno-α-aminocarboxylic acid, the reaction mixture is preferably adjusted to weak acidity to neutrality, specifically to the vicinity of the isoelectric point of the β-halogeno-α-aminocarboxylic acid. When the β-halogeno-α-aminocarboxylic acid is an α-amino-β-halopropionic acid or α-amino-β-halobutyric acid, the pH is preferably adjusted to about 4 to 7.

Specifically, in a simple procedure, taken as an example, for isolating the above β-halogeno-α-aminocarboxylic acid in its free form, those relatively low boiling components remaining in the reaction mixture after the halogenation reaction, such as sulfur dioxide, excess hydrogen halide (e.g. hydrogen chloride) and unreacted halogenating agent (e.g. thionyl halide), are preferably reduced in amount or removed in advance, the pH is then adjusted at a low temperature using a basic lithium compound such as lithium hydroxide or lithium carbonate, preferably lithium hydroxide, a small amount (preferably minimum amount) of water, and the resulting precipitate, i.e. β-halogeno-α-aminocarboxylic acid, is collected using a medium mainly comprising a water miscible organic solvent used as the halogenation reaction solvent, preferably a water-miscible ether solvent. Alternatively, after reducing or removing in advance those relatively low boiling components remaining in the reaction mixture after the halogenation reaction, such as sulfur dioxide, the excess hydrogen halide (e.g. hydrogen chloride) and the unreacted halogenating agent (e.g. thionyl halide), the reaction solvent is replaced with a small amount (preferably minimum amount) of water at a low temperature and, if necessary after treatment with an adsorbent such as activated carbon and/or separation of the insoluble matter by filtration for the purpose of removing impurities and/or decoloration, the pH is adjusted using a basic lithium compound such as lithium hydroxide or lithium carbonate, preferably lithium hydroxide and a small amount (preferably minimum amount) of water, the precipitation of the β-halogeno-α-aminocarboxylic acid is fully caused by combinedly using the above water-miscible organic solvent, preferably acetone; said acid can then be recovered.

In cases where the above β-halogeno-α-aminocarboxylic acid is submitted to the next step without isolation, those relatively low boiling components remaining in the reaction mixture after the halogenation reaction, such as sulfur dioxide, the excess hydrogen halide (e.g. hydrogen chloride) and the unreacted halogenating agent (e.g. thionyl halide), are reduced or removed beforehand, and the reaction solvent is replaced with water at a low temperature, for instance, and, if necessary the pH is adjusted with a base such as sodium hydroxide or lithium hydroxide and, further, if necessary treatment with an adsorbent such as activated carbon and/or separation of the insoluble matter by filtration is conducted for the purpose of removing impurities and/or decoloration, whereafter the above β-halogeno-α-aminocarboxylic acid can be used in the form of an aqueous solution.

A preferred method of purifying and isolating the above β-halogeno-α-aminocarboxylic acid is now described. This is a method of purifying and isolating the β-halogeno-α-aminocarboxylic acid in its free form. In the method (1) mentioned below, the β-halogeno-α-aminocarboxylic acid can be used and, in the method (2) mentioned below, the β-halogeno-α-aminocarboxylic acid or a salt thereof can be used, and the salt of the β-halogeno-α-aminocarboxylic acid is preferably a hydrohalogenic acid salt such as hydrochloride. It is of course possible to use an optically active form of the above β-halogeno-α-aminocarboxylic acid.

(1) Using water as a good solvent and a water-miscible organic solvent as a poor solvent, the β-halogeno-α-aminocarboxylic acid is caused to crystallize out. Preferably, the β-halogeno-α-aminocarboxylic acid is caused to crystallize out from an aqueous solution thereof in the presence of a water-miscible organic solvent. If necessary, treatment with an adsorbent such as activated carbon and/or filtration of the insoluble matter may be combined for the purpose of removing impurities and/or decoloration.

(2) Treatment of the aqueous solution containing the β-halogeno-α-aminocarboxylic acid and hydrogen halide with a basic lithium compound, such as lithium hydroxide or lithium carbonate, for converting the (hydrohalogenic) acid to the salt is combined with precipitation of the β-halogeno-α-aminocarboxylic acid in its free form using water as a good solvent and a water-miscible organic solvent as a poor solvent. Basically, the above-mentioned technique for isolating the β-halogeno-α-aminocarboxylic acid in its free form from the halogenation reaction mixture can be utilized. Preferably, the β-halogeno-α-aminocarboxylic acid or a salt thereof (preferably a hydrohalogenic acid salt such as hydrochloride) is first caused to coexist with, preferably dissolved in, an aqueous solution of a hydrohalogenic acid, such as hydrochloric acid, or water. The pH is adjusted generally to 3 or below, preferably to 2 or below, and the amount of water required for fluidization, preferably dissolution is preferably minimized. Then, if necessary, treatment with an adsorbent such as activated carbon and/or insoluble matter separation by filtration is carried out for the purpose of removing impurities and/or decoloration. While adjusting the pH with a basic lithium compound such as lithium hydroxide or lithium carbonate, the hydrohalogenic acid is converted to a salt (a lithium halide such as lithium chloride) soluble in the organic solvent and water, and the β-halogeno-α-aminocarboxylic acid is caused to precipitate using the water-miscible organic solvent as a poor solvent while the above salt is caused to remain dissolved without precipitation. Thereafter, the acid is recovered by a conventional solid-liquid separation procedure, such as filtration or centrifugation. Alternatively, the β-halogeno-α-aminocarboxylic acid or a salt thereof (preferably a hydrohalogenic acid salt thereof, such as hydrochloride) is dissolved in a medium comprising water or an aqueous solution of a hydrohalogenic acid, such as hydrochloric acid, and an organic solvent miscible with water. The pH after dissolution is adjusted generally to 3 or below, preferably to 2 or below. Then, if necessary, treatment with an adsorbent such as activated carbon and/or insoluble matter separation by filtration is carried out for the purpose of removing impurities and/or decoloration. The β-halogeno-α-aminocarboxylic acid is caused to precipitate by adjusting the pH (converting the hydrohalogenic acid, if present, to the form of a salt) using a basic lithium compound such as lithium hydroxide or lithium carbonate while the above salt formed (lithium halide such as lithium chloride) is caused to remain dissolved without precipitation. Thereafter, the desired acid is recovered by a conventional solid-liquid separation procedure such as filtration or centrifugation.

The water-miscible organic solvent to be used in the above methods (1) and (2) specifically includes, but is not limited to, 1,2-dimethoxyethane, 1,4-dioxane, tetrahydrofuran, diethylene glycol dimethyl ether, triethylene glycol dimethyl ether, tetraethylene glycol dimethyl ether, polyethylene glycol dimethyl ether, acetonitrile, methanol, ethanol, n-propanol, isopropanol, tert-butanol and acetone, among others. Among these, acetone, in particular, is preferred from the viewpoint of increased precipitation of the β-halogeno-α-aminocarboxylic acid, which is a water-soluble compound, obtaining crystals with good characteristics, ease of handling and inexpensiveness, among others.

Since the β-halogeno-α-aminocarboxylic acid has a high solubility in water, it is desirable, for attaining increased precipitation, to reduce the amount of water, use the above water-miscible organic solvent in a volume ratio of not less than 1 relative to water and maintain the final cooling temperature at a low level, preferably not higher than 10° C., more preferably not higher than 0° C. The solubility of the above β-halogeno-α-aminocarboxylic acid tends to increase in the presence of lithium chloride or the like, hence it is effective to use acetone combinedly so that the precipitation may be maximized.

In the step of crystallization or precipitation of the above β-halogeno-α-aminocarboxylic acid, the pH is adjusted to weak acidity to neutrality, specifically to the vicinity of the isoelectric point of the β-halogeno-α-aminocarboxylic acid. When the β-halogeno-α-aminocarboxylic acid is an α-amino-β-halopropionic acid or α-amino-β-halobutyric acid, the pH is preferably adjusted to about 4 to 7.

Most preferred as the above hydrohalogenic acid is hydrogen chloride (hydrochloric acid) and, as the above basic lithium compound, lithium hydroxide or lithium carbonate, in particular lithium hydroxide, is preferred.

Since the above β-halogeno-α-aminocarboxylic acid is not always stable, care is preferably taken in contacting the same with a base so as to effect contacting thereof with water or an aqueous medium approximately under acidic or neutral conditions, for instance. Generally, the acid is handled preferably under acidic to neutral conditions, for example at a pH of not higher than 7, and at low temperatures.

According to the method of the present invention, β-halogeno-α-aminocarboxylic acids can efficiently be synthesized from β-hydroxy-α-aminocarboxylic acids in one reaction step, and high quality β-halogeno-α-aminocarboxylic acids or salts thereof can be isolated in high yields. Further, when the above reaction is carried out using the β-hydroxy-α-aminocarboxylic acid in an optically active form, the corresponding optically active β-halogeno-α-aminocarboxylic acid having the same configuration as that of the substrate can be obtained while the optical purity of the starting material is substantially maintained without accompanying substantial racemization.

For converting the optically active β-chloroalanine obtained from an optically active serine or a salt thereof according to the above production method to an optically active N-protected-S-phenylcysteine, two methods are conceivable, one comprising treatment with an amino-protecting agent, followed by thiophenylation and the other comprising treatment with an amino-protecting agent following thiophenylation. However, studies made by the present inventors revealed that the method comprising treatment with an amino-protecting agent followed by thiophenylation is preferred from the viewpoint of yield and operability. The method comprising treatment with an amino-protecting agent following thiophenylation cannot give satisfactory yields since the optically active β-chloroalanine is unstable particularly under thiophenylation conditions.

The method of the present invention for producing the optically active N-protected-β-chloroalanines of the general formula (2) given above or salts thereof comprises producing an optically active β-chloroalanine or a salt thereof by treating an optically active serine or a salt of an optically active serine with an acid with a chlorinating agent and then treating that product with an amino-protecting agent. In this production method, the reaction for obtaining the optically active β-chloroalanine or a salt thereof can be carried out in the same manner as mentioned above.

In the above general formula (2), $R^1$ represents an amino-protecting group. As the amino-protecting group, there may be mentioned those described in Theodora W. Green: Protective Groups in Organic Synthesis, 2nd edition, John Wiley & Sons, published 1990, such as benzyloxycarbonyl, ethoxycarbonyl, methoxycarbonyl, tert-butoxycarbonyl, acetyl, tosyl, benzoyl, phthaloyl and the like. The range of choice also includes such protective groups as (3S)-tetrahydrofuranyloxycarbonyl, 3-hydroxy-2-methylbenzoyl whose hydroxyl group may optionally be protected, and the like. However, benzyloxycarbonyl is preferred among others.

In the above general formula (2), $R^0$ generally represents a hydrogen atom but may also represent such an amino-protecting group as phthaloyl together with $R^1$.

The above amino-protecting agent corresponds to the above amino-protecting group and includes conventional amino-protecting agents without any particular restriction. Thus, mention maybe made of, for example, benzyl chloroformate, ethyl chloroformate, methyl chloroformate, di-tert-butyl dicarbonate, benzoyl chloride, acetyl chloride, p-toluenesulfonyl chloride, phthalic anhydride, and N-carboethoxyphthalimide. The range of choice further includes (3S)-tetrahydrofuranyl chloroformate, 3-hydroxy-2-methylbenzoyl chloride whose hydroxyl group may optionally be protected, and the like. Among them, benzyl chloroformate is preferred.

While the treatment with the above amino-protecting agent may be carried out using an optically active β-chloroalanine isolated, it is preferred that the amino group protection be effected by treating, with the above amino-protecting agent, an aqueous medium containing an optically active β-chloroalanine as obtained in the manner mentioned above. In either case, abase is used and the base to be used is, for example, sodium hydroxide or potassium carbonate. The above treatment with an amino-protecting agent may be carried out in any medium comprising water and/or an organic solvent.

The solvent to be used in that case is not particularly restricted but may be, for example, 1,2-dimethoxyethane, 1,4-dioxane, tetrahydrofuran, diethylene glycol dimethyl ether, triethylene glycol dimethyl ether, tetraethylene glycol dimethyl ether, polyethylene glycol dimethyl ether, tert-butyl methyl ether, dibutyl ether, diethyl ether or a like other ether solvent; acetonitrile, methylene chloride, ethyl acetate, acetone, toluene or a like other aprotic solvent.

Taking carbobenzyloxylation as an example, the method for the above amino group protection is now specifically described. To an aqueous medium containing an optically active β-chloroalanine, for instance, there is added benzyl chloroformate in an amount of 1 to 2 molar equivalents, preferably about 1.0 molar equivalent, relative to the substrate, at a temperature at which the solvent will not freeze, up to 30° C., more preferably at a temperature not higher than 5° C., while maintaining the pH at 8 to 13, preferably 9 to 12, more preferably 9 to 10, by adding a base, such as sodium hydroxide or potassium carbonate, and the resulting mixture is stirred at a temperature at which the solvent will not freeze, up to 30° C., more preferably at a temperature not higher than 5° C., preferably for 1 to 30 hours. If necessary, the reaction mixture may be washed with an organic solvent immiscible with water or with an aqueous medium, for example toluene, for the purpose of removing the unreacted portion of benzyl chloroformate and the byproduct benzyl alcohol.

The optically active N-protected-β-chloroalanine produced in the above manner can be isolated, for example by a conventional extraction procedure followed by column chromatography.

The method of the present invention for producing optically active N-protected-S-phenylcysteines of the above general formula (3) or salts thereof comprises treating an optically active serine or a salt of an optically active serine with an acid with a chlorinating agent, then treating the thus-obtained optically active β-chloroalanine with an amino-protecting agent, and further reacting the resulting optically active N-protected-β-chloroalanine or a salt thereof with thiophenol under a basic condition. In the above general formula (3), $R^0$ and $R^1$ are the same as the $R^0$ and $R^1$ specifically mentioned above. In this production method, the reactions for the production of the optically active N-protected-β-chloroalanine or a salt thereof can be carried out in the same manner as mentioned above.

The thiophenylation of the above optically active N-protected-β-chloroalanine can be carried out using an optically active N-protected-β-chloroalanine isolated in the manner mentioned above. It is also possible to adjust the pH of the reaction mixture after amino-protecting agent treatment, add thiophenol directly thereto and effecting the reaction in that reaction mixture.

The above step of reacting the optically active N-protected-β-chloroalanine with thiophenol can be conducted in water and/or an organic solvent under a basic condition. The organic solvent is not particularly restricted but includes, for example, ether solvents such as 1,2-dimethoxyethane, 1,4-dioxane, tetrahydrofuran, diethylene glycol dimethyl ether, triethylene glycol dimethyl ether, tetraethylene glycol dimethyl ether, polyethylene glycol dimethyl ether, tert-butyl methyl ether, dibutyl ether and diethyl ether; and other aprotic solvents such as acetonitrile, methylene chloride, ethyl acetate, acetone and toluene, among others.

The above thiophenol is used generally in an amount of 1 to 5 molar equivalents, preferably 1 to 3 molar equivalents, more preferably about 1.5 molar equivalents, relative to the optically active N-protected-β-chloroalanine.

For effecting the above thiophenylation under a basic condition, an inorganic base or the like is preferably added as a base. The inorganic base is not particularly restricted but may be, for example, sodium hydrogen carbonate, potassium hydrogen carbonate, sodium carbonate, potassium carbonate or sodium hydroxide. An alkaline pH buffering agent may also be used.

The amount of the above base to be used may vary depending on the species thereof. In the case of sodium hydroxide or sodium carbonate, for instance, it is used in an amount of 1 to 5 molar equivalents, preferably 1 to 3 molar equivalents, relative to the optically active N-protected-β-chloroalanine. The pH of the reaction mixture is preferably about 9 to 11. Under strongly alkaline conditions, the yield tends to decrease due to side reactions. After completion of the reaction, the product can be isolated, for example by acidifying the reaction mixture with hydrochloric acid, sulfuric acid or the like, extracting the mixture with an organic solvent such as ethyl acetate, concentrating the extract and subjecting the concentrate to column chromatography, for instance.

The above thiophenylation can be effected, for example by adding a base such as sodium hydroxide and sodium carbonate to a solution composed of an optically active N-protected-β-chloroalanine and an amount of water to give a starting material concentration of 5 to 30% (w/v), preferably at 0 to 30° C., to thereby preferably adjust the pH to 9 to 11, and further adding thiophenol in an amount of 1 to 5 molar equivalents, preferably 1 to 3 molar equivalents, relative to the optically active N-protected-β-chloroalanine, followed by stirring preferably at 30 to 90° C., more preferably 40 to 70° C. The order of addition of the reagents is not always restricted to the one mentioned above. For example, the thiophenylation can also be effected by adding a base to an aqueous solution containing thiophenol and an optically active N-protected-β-chloroalanine or by adding thiophenol and a base simultaneously to an aqueous solution of an optically active N-protected-β-chloroalanine.

In the production method of the present invention, by conducting, without isolating the intermediates, the three steps, namely the step of treating an optically active serine or a salt of an optically active serine with an acid with a chlorinating agent, the step of treating the resulting optically active β-chloroalanine with an amino-protecting agent and the step of reacting the resulting optically active N-protected-β-chloroalanine with thiophenol under a basic condition, it is possible to obtained the corresponding optically active N-protected-S-phenylcysteine derivative in a simple and efficient manner. It is also possible to conduct, without isolating the intermediate, the two steps, namely the step of treating an optically active β-chloroalanine with an amino-protecting agent and the step of reacting the resulting optically active N-protected-β-chloroalanine with thiophenol under a basic condition.

The optically active N-protected-S-phenylcysteine obtained from the corresponding optically active serine or a salt thereof by the production method of the present invention has an optical purity as high as 98% e.e. at the step prior to purification by crystallization, for instance. Thus, according to the present invention, an optically active N-protected-S-phenylcysteine having the same configuration as that of the substrate can be produced from the optically active serine or a salt thereof while substantially maintaining the optical purity thereof without accompanying substantial racemization.

The optically active N-protected-S-phenylcysteine, in particular N-carbobenzyloxy-S-phenyl-L-cysteine, is a compound very useful as an intermediate of HIV protease inhibitors (WO 9532185), for instance.

BEST MODES FOR CARRYING OUT THE INVENTION

The following examples illustrate the present invention in further detail. They are, however, by no means limitative of the scope of the present invention.

EXAMPLE 1

Production of β-chloro-L-alanine Hydrochloride

L-Serine (5.0 g, 0.0476 mol) was added to 50 ml of 1,4-dioxane, and hydrogen chloride gas was introduced into the resulting solution with stirring at room temperature. On that occasion, the hydrogen chloride in the solution amounted to 14.5 g (0.3977mol). To the solution was added slowlyl 2.5 g (0.1051 mol) of thionyl chloride, and the reactor inside temperature was then adjusted to 50° C. After about 6 hours of stirring, this solution was concentrated to about half the original volume. The concentrate was cooled to 0 to 10° C., and 50 ml of water was added gradually so as to maintain this temperature. HPLC analysis of this solution revealed the formation of 6.9 g (0.0431 mol) of β-chloro-L-alanine hydrochloride (yield: 91 mole %).

EXAMPLE 2

Production of β-chloro-L-alanine Hydrochloride

L-Serine (5.0 g, 0.0476 mol) was added to 50 ml of 1,4-dioxane, and hydrogen chloride gas was introduced into the resulting solution with stirring at room temperature. On that occasion, the hydrogen chloride in the solution amounted to 11.2 g (0.3072 mol) . To the solution was added slowly 6.2 g (0.0521 mol) of thionyl chloride, and the reactor inside temperature was then adjusted to 45° C. After about 20 hours of stirring, this solution was concentrated to about half the original volume. The concentrate (slurry) was filtered, the cake was washed with 10 ml of 1,4-dioxane and the wet crystals were dried under reduced pressure (40° C., not higher than 10 mm Hg) to give dry crystals. HPLC analysis of the crystals obtained revealed that the yield of β-chloro-L-alanine hydrochloride as pure substance was 7.2 g (0.0450 mol).

The IR, $^1$H-NMR and $^{13}$C-NMR data of the β-chloro-L-alanine hydrochloride obtained were in complete agreement with those of the β-chloro-L-alanine hydrochloride purchased from Aldrich Chemical Co.

EXAMPLE 3

Production of β-chloro-L-alanine

Milk white crystals (purity 95.2% by weight, containing 3.6 g (0.0225 mol) of β-chloro-L-alanine hydrochloride) obtained in the same manner as in Example 2 were added to 14 ml of water to give a slurry. This slurry was completely dissolved by slowly adding about 2 g of concentrated hydrochloric acid. To the solution was added 0.1 g of 50% activated carbon, and the mixture was stirred at room temperature for about 10 minutes. The activated carbon was filtered off under reduced pressure and washed with 1 ml of water. The filtrate and washings obtained were cooled to 0 to 10° C., and the pH was adjusted to 5.5 by gradually adding a saturated aqueous solution of lithium hydroxide while maintaining that temperature, to give a slurry. Acetone (42 ml) was gradually added to this slurry to thereby cause sufficient precipitation of crystals, the resulting mixture was cooled to −10 to 0° C. and maintained at that temperature for about 1 hour. The precipitate crystals were filtered off, the cake was washed with 14 ml of acetone, and the wet crystals obtained were dried under reduced pressure (40° C., not higher than 10 mm Hg) to give 2.65 g of β-chloro-L-alanine as white crystals. HPLC analysis of these crystals revealed a purity of 99.9% by weight and a yield of pure β-chloro-L-alanine of 2.65 g (0.0214 mol).

The β-chloro-L-alanine obtained had an optical purity of not less than 99.9% e.e. as determined by HPLC analysis under the conditions shown below.

<Analytical Conditions>
Column: Tosoh TSK-Gel Enantio L1 (4.6 mm×250 mm)
Mobile phase: 0.5 M $CUSO_4$ aq./acetonitrile=80/20
Column temperature: 40 ° C.
Detection wavelength: 254 nm
Flow rate: 1.0 ml/min
Retention time:
  β-chloro-L-alanine 9.3 min
  β-chloro-D-alanine 7.8 min

EXAMPLE 4

Production of β-chloro-L-alanine

L-Serine (30.0 g, 0.2855 mol) was added to 600 ml of 1,4-dioxane, and hydrogen chloride gas was introduced into the resulting solution with stirring at room temperature. On that occasion, the hydrogen chloride in the solution amounted to 133.1 g (3.6508 mol) To the solution was added slowly 40.8 g (0.3426 mol) of thionyl chloride, and the reactor inside temperature was then adjusted to 40° C. After about 20 hours of stirring, the liquid (slurry) was concentrated to about half the original volume. The concentrate (slurry) was cooled to 0 to 10° C., and 200 ml of water was added gradually so as to maintain that temperature, to thereby cause dissolution of the precipitate. The resulting solution was further concentrated until the weight became about 200 g, 3.0 g of 50% activated carbon was then added, and the mixture was stirred at room temperature for about 10 minutes. The activated carbon was filtered off under reduced pressure and washed with 10 ml of water. The filtrate and washings obtained were combined and further concentrated to a weight of about 120 g. This concentrate was cooled to 0 to 10° C., and the pH was adjusted to 5.5 by gradually adding a saturated aqueous solution of lithium hydroxide while maintaining that temperature, to give a slurry. To this slurry was gradually added 600 ml of acetone for effecting sufficient precipitation of crystals, and the slurry was then cooled to −10 to 0° C. and maintained at this temperature for about 1 hour. The precipitate crystals were filtered off under reduced pressure and the cake was washed with 100 ml of acetone. The wet crystals thus obtained were dried under reduced pressure (40° C., not higher than 10 mm Hg) to give 32.6 g of β-chloro-L-alanine as dry crystals. HPLC analysis of the crystals revealed a purity of 99.8% by weight and a yield of pure β-chloro-L-alanine of 32.5 g (0.2625 mol)

EXAMPLE 5

Production of β-chloro-D-alanine Hydrochloride

D-Serine (5.0 g, 0.0476 mol) was added to 50 ml of 1,4-dioxane, and hydrogen chloride gas was introduced into the resulting solution with stirring at room temperature. On that occasion, the hydrogen chloride in the solution amounted to 11.5 g (0.3154 mol). To the solution was added slowly 6.2 g (0.0521 mol) of thionyl chloride, and the reactor inside temperature was then adjusted to 45° C. After about 20 hours of stirring, this solution was concentrated to about half the original volume. The concentrate (slurry) was filtered, the cake was washed with 10 ml of 1,4-dioxane and the wet crystals were dried under reduced pressure (40° C., not higher than 10 mm Hg) to give dry crystals. HPLC analysis of the crystals obtained revealed that the yield of β-chloro-D-alanine hydrochloride as pure substance was 7.0,g (0.0438 mol). The thus-obtained β-chloro-D-alanine hydrochloride had an optical purity of not less than 99.9% e.e. as determined by the same method as mentioned in Example 3.

EXAMPLE 6

Production of β-chloro-L-alanine Hydrochloride

L-Serine (5.0 g, 0.0476 mol) was added to 50 ml of each of the reaction solvents specified in Table 1, and hydrogen chloride gas was introduced into the resulting solution with stirring at room temperature until saturation with hydrogen chloride. To the solution was added slowly 12.5 g (0.1051 mol) of thionyl chloride, and the reaction was effected under the conditions shown in Table 1. The reaction mixture (slurry) was concentrated to about half the original volume. The concentrate was cooled to 0 to 10° C. and 50 ml of water was added slowly so as to maintain this temperature. This solution was analyzed by HPLC and the yield as β-chloro-L-alanine hydrochloride was determined. The results thus obtained are shown in Table 1.

TABLE 1

| Reaction Solvent | Reaction temperature | Reaction time | Yield |
| --- | --- | --- | --- |
| 1,2-Dimethoxyethane | 50° C. | 10 hrs | 97% |
| Tetrahydrofuran | 40° C. | 30 hrs | 92% |
| Triethylene glycol Dimethylether | 50° C. | 10 hrs | 93% |

EXAMPLE 7

Production of (αS, βR)-α-amino-β-chlorobutyric Acid Hydrochloride

L-Threonine (10.14 g, 0.0851 mol) was added to 100 ml of 1,4-dioxane, and hydrogen chloride gas was introduced into the resulting solution with stirring at room temperature. On that occasion, the hydrogen chloride in the solution amounted to 15.5 g (0.4251mol). To the solution was added slowly 12.2 g (0.1022 mol) of thionyl chloride, and the reactor inside temperature was then adjusted to 50° C. After about 10 hours of stirring, this solution was concentrated to about half the original volume. The concentrate (slurry) was filtered, the cake was washed with 20 ml of 1,4-dioxane and the wet crystals were dried under reduced pressure (40° C., not higher than 10 mm Hg) to give dry crystals. HPLC analysis of the crystals obtained revealed that the yield of (αS, βR)-α-amino-β-chlorobutyric acid hydrochloride as pure substance was 12.2 g (0.0701 mol). $[\alpha]_D^{20}+16.1°$ (c=1.0, water) (lit., $[\alpha]_D^{20}+17.8°$ (c=1.0, water) [CHIRALITY 9, 656–660 (1997)].

EXAMPLE 8

Production of (αS, βR)-α-amino-β-hydroxybutyric Acid

Milk white crystals [purity 94.9% by weight, containing 5.0 g (0.0287 mol) of (αS, βR)-α-amino-β-hydroxybutyric acid hydrochloride] obtained in the same manner as in Example 7 were added to 19 ml of water to give a slurry. This slurry was completely dissolved by slowly adding about 2.8 g of concentrated hydrochloric acid. To the solution was added 0.1 g of 50% activated carbon, and the mixture was stirred at room temperature for about 10 minutes. The activated carbon was filtered off under reduced pressure and washed with 1 ml of water. The filtrate and washings obtained were combined and cooled to 0 to 10° C., and the pH was adjusted to 5.5 by gradually adding a saturated aqueous solution of lithium hydroxide while maintaining that temperature, to give a slurry. Acetone (58 ml) was gradually added to this slurry to thereby cause sufficient precipitation of crystals, the resulting mixture was cooled to −10 to 0° C. and maintained at that temperature for about 1 hour. The precipitate crystals were filtered off, the cake was washed with 19 ml of acetone, and the wet crystals obtained were dried under reduced pressure (40° C., not higher than 10 mm Hg) to give 3.75 g of (αS, βR)-α-amino-β-chlorobutyric acid as white crystals. HPLC analysis of these crystals revealed a purity of 99.8% by weight and a yield of pure (αS, βR)-α-amino-β-chlorobutyric acid of 3.74 g (0.02272 mol). mp 176° C. (decomp.) (lit., mp 176° C. (decomp.) [Yakugaku Kenkyu, 33, 428–437 (1961)].

The IR, $^1$H-NMR and $^{13}$C-NMR data of the (αS, βR)-β-amino-β-chlorobutyric acid thus obtained as crystals were in complete agreement with those of the crystalline (αS, βR)-α-amino-β-chlorobutyric acid separately synthesized by the method mentioned below.

Reference Example 1

Alternative Synthesis of (αS, βR)-α-amino-β-chlorobutyric Acid

Using thionyl chloride and methanol, threonine was derivatized into threonine methyl ester hydrochloride, which was then treated with thionyl chloride to give α-amino-β-chlorobutyric acid methyl ester hydrochloride. This was then converted to α-amino-β-chloropropionic acid hydrochloride by hydrolyzing with hydrochloric acid. The α-amino-β-chloropropionic acid hydrochloride was crystallized and isolated by the same technique as mentioned in Example 8.

EXAMPLE 9

Production of β-chloro-L-alanine Hydrochloride

L-Serine hydrochloride (6.7 g, 0.0473 mol) was added to 50 ml of 1,4-dioxane. To the solution was added slowly 6.8 g (0.0572 mol) of thionyl chloride at room temperature, and the reactor inside temperature was then adjusted to 60° C. After about 3 hours of stirring, this solution was concentrated to about half the original volume. The concentrate was cooled to 0 to 10° C., and 50ml of water was added gradually so as to maintain this temperature. HPLC analysis of this solution revealed the formation of 4.6 g (0.0287 mol) of β-chloro-L-alanine hydrochloride (yield 61 mole %).

Comparative Example 1

L-Serine (20.0 g, 0.1903 mol) was added to 49.8 g (0.4187 mol) of thionyl chloride, and the mixture was warmed to 60° C. and stirred for 6 hours. This solution was hydrolyzed and then analyzed by HPLC. No β-chloro-L-alanine peak was observed but peaks due to unreacted L-serine and various impurities were observed.

Comparative Example 2

L-Serine (15.0 g, 0.1427 mol) was added to 150 ml of toluene, and hydrogen chloride gas was blown into the resulting solution at room temperature until saturation. To this solution was added 37.4 g (0.3140 mol) of thionyl chloride, and the mixture was then warmed to 80° C. and stirred for 20 hours, This solution was hydrolyzed and then analyzed by HPLC. Peaks of various impurities were observed and the peak of β-chloro-L-alanine corresponded only to a trace amount. (The above reaction mixture contained a tar-like substance and had a deep black color.)

Comparative Example 3

L-Serine (15.0 g, 0.1427 mol) was added to 150 ml of methylene chloride, and hydrogen chloride gas was blown into the resulting solution at room temperature until saturation. To this solution was added 37.4 g (0.3140 mol) of thionyl chloride, and the mixture was then warmed to 40° C. and stirred for 16 hours, This solution was hydrolyzed and then analyzed by HPLC. Peaks of various impurities were observed and the peak of β-chloro-L-alanine corresponded only to a trace amount. (The above reaction mixture contained a tar-like substance and had a deep black color.)

EXAMPLE 10

Production of N-carbobenzyloxy-β-chloro-L-alanine

L-Serine hydrochloride (0.4 g, 2.84 mmol) and 0.029 g (0.28 mmol) of triethylamine were suspended in 4 ml of diethylene glycol dimethyl ether. Thereto was added dropwise 0.67 g (5.68 mmol) of thionyl chloride at room temperature in a nitrogen gas atmosphere. After 2 hours of stirring at 60° C., 8 ml of water was added while maintaining the reaction mixture inside at 15° C. or below, and the whole mixture was stirred at room temperature for 30 minutes. Further, 1.6 g of potassium carbonate was added to make the pH about 10 and, thereafter, 0.956 g (5.68 mmol) of benzyl chloroformate was added dropwise. After overnight standing at room temperature, the reaction mixture was washed with ethyl acetate, the aqueous layer obtained was cooled with ice and acidified with 50% sulfuric acid and then extracted with ethyl acetate. The solvent was distilled off and the residue was purified by column chromatography to give 0.3 g (1.16 mmol, 41%) of N-carbobenzyloxy-β-chloro-L-alanine.

The N-carbobenzyloxy-β-chloro-L-cysteine obtained gave the following $^1$H-NMR and IR data.

$^1$H-NMR (400 MHz, CDCl$_3$) δ(ppm): 3.85–4.06 (m, 2H) , 4.80–4.82 (m, 1H), 5.14 (s, 2H), 5.70 (d, J=7.8 Hz, 1H), 7.36 (s, 5H) IR (neat): 3034, 1720, 1516, 1456, 1203, 1066, 855, 754, 698 (cm$^{-1}$)

EXAMPLE 11

Production of N-carbobenzyloxy-β-chloro-L-alanine

L-Serine hydrochloride (0.4 g, 2.84 mmol) and 0.029 g (0.28 mmol) of triethylamine were suspended in 4 ml of 1,2-dimethoxyethane. Thereto was added dropwise 0. 67 g (5.68 mmol) of thionyl chloride at room temperature in a nitrogen gas atmosphere. After 2 hours of stirring at 60° C., 8 ml of water was added while maintaining the reaction mixture inside at 15° C. or below, and the whole mixture was stirred at room temperature for 30 minutes. Further, 1.6 g of potassium carbonate was added to make the pH about 10 and, thereafter, 0.956 g (5.68 mmol) of benzyl chloroformate was added dropwise. After overnight standing at room temperature, the reaction mixture was cooled with ice and acidified with 50% sulfuric acid. The solution obtained was analyzed by HPLC, which revealed the formation of N-carbobenzyloxy-β-chloro-L-alanine in a yield of 42% (1.18 mmol) . The analytical conditions were as shown below.

Analytical conditions (N-carbobenzyloxy-β-chloro-L-alanine/N-carbobenzyloxy-L-serine)
Column: YMC-Pack ODS-A A-303 (250 mm×4.6 mm)
Mobile phase: Phosphate buffer (pH=3.0):acetonitrile= 60:40
Flow rate: 1.0 ml/min
Sample injection size: 20 μl
Sample solvent: acetonitrile
Retention time:
  6.2 min (N-carbobenzyloxy-β-chloro-L-alanine)
  3.9 min (N-carbobenzyloxy-L-serine)

EXAMPLE 12

Production of N-carbobenzyloxy-β-chloro-L-alanine

L-Serine hydrochloride (0.1 g, 0.71mmol) and7.2mg (0.07 mmol) of triethylamine were suspended in a solvent composed of 1 ml of acetonitrile and 0.1 ml of diethylene glycol dimethyl ether. Thereto was added dropwise 0.167 g (1.42 mmol) of thionyl chloride at room temperature in a nitrogen gas atmosphere. After 2 hours of stirring at 60° C., 2 ml of water was added while maintaining the reaction mixture inside at 15° C. or below, and the whole mixture was stirred at room temperature for 30 minutes. Further, 0.4 g of potassium carbonate was added to make the pH about 10 and, thereafter, 0.239 g (1.52 mmol) of benzyl chloroformate was added dropwise. After overnight standing at room temperature, the reaction mixture was cooled with ice and acidified with 50% sulfuric acid. The solution obtained was analyzed by HPLC by the same procedure as mentioned in Example 11, which revealed the formation of N-carbobenzyloxy-β-chloro-L-alanine in a yield of 34% (0.24 mmol).

EXAMPLE 13

Production of N-carbobenzyloxy-S-phenyl-L-cysteine

N-Carbobenzyloxy-β-chloro-L-alanine (0.108 g, 0.42 mmol) was dissolved in 0.5 ml of water and, then, 0.097 g (0.92 mmol) of sodium carbonate was added. Thereafter, 0.054 g (0.50 mmol) of thiophenol was added dropwise at room temperature in a nitrogen gas atmosphere. After 2 hours of stirring at 60° C., the reaction mixture was cooled with ice and acidified with 1 N hydrochloric acid, and then extracted with ethyl acetate. The solvent was distilled off and the residue was purified by column chromatography to give 0.112 g (0.34 mmol, 81%) of N-carbobenzyloxy-S-phenyl-L-cysteine. The compound obtained had an optical purity of not less than 98% e.e. The optical purity was determined by HPLC. The analytical conditions are shown below.

Optical purity determination conditions (N-carbobenzyloxy-S-phenyl-L-cysteine/N-carbobenzyloxy-S-phenyl-D-cysteine)
Column: DAICEL CHIRALPAK AS (250 mm×4.6 mm)
Mobile phase: (hexane/tert-butyl methyl ether/tri-fluoroacetic acid =800/200/2):ethanol=85:15
Flow rate: 1.2 ml/min
Sample injection size: 10 μl
Temperature: 35° C.
Sample solvent: (hexane/tert-butyl methyl ether/tri-fluoroacetic acid=800/200/2):ethanol=80:20
Retention time:
  4.5 min (N-carbobenzyloxy-S-phenyl-L-cysteine)
  5.6 min (N-carbobenzyloxy-S-phenyl-D-cysteine)

The results of ¹H-NMR and IR analysis of the N-carbobenzyloxy-S-phenyl-L-cysteine obtained were as follows:
¹H-NMR (400 MHz, CDCl₃) δ(ppm): 3.41 (dd, J=5.1, 14.2 Hz, 2H), 4.61–4.63 (m, 1H), 5.07 (s, 2H), 5.56 (d, J=7.3 Hz, 1H), 7.17–7.55 (m, 10H) IR (neat): 3036, 1686, 1532, 1281, 1059, 737 (cm⁻¹)

EXAMPLE 14

Production of N-carbobenzyloxy-S-phenyl-L-cysteine

N-Carbobenzyloxy-β-chloro-L-alanine (0.091 g, 0.35 mmol) was dissolved in 0.45 ml of water and, then, 0.065 g (0.77 mmol) of sodium hydrogen carbonate was added. Thereafter, 0.046 g (0.42 mmol) of thiophenol was added dropwise at room temperature in a nitrogen gas atmosphere. After 2 hours of stirring at 60° C., the reaction mixture was cooled with ice and acidified with 1 N hydrochloric acid, and then extracted with ethyl acetate. The solvent was distilled off and the residue was purified by column chromatography to give 0.097 g (0.29mmol, 84%) of N-carbobenzyloxy-S-phenyl-L-cysteine. The product obtained had an optical purity of not less than 98% e.e. as determined by HPLC analysis following the same procedure as in Example 13.

EXAMPLE 15

Production of N-carbobenzyloxy-S-phenyl-L-cysteine

N-Carbobenzyloxy-β-chloro-L-alanine (0.137 g, 0.53 mmol) was dissolved in 0.68 ml of water and, then, 0.58 ml of 2 N aqueous sodium hydroxide was added. Thereafter, 0.069 g (0.63 mmol) of thiophenol was added dropwise at room temperature in a nitrogen gas atmosphere. After 2 hours of stirring at 60° C., the reaction mixture was cooled with ice and acidified with 1 N hydrochloric acid, and then extracted with ethyl acetate. The solvent was distilled off and the residue was purified by column chromatography to give 0.107 g (0.32 mmol, 61%) of N-carbobenzyloxy-S-phenyl-L-cysteine. The product obtained had an optical purity of not less than 98% e.e. as determined by HPLC analysis in the same manner as in Example 13.

EXAMPLE 16

Production of N-carbobenzyloxy-S-phenyl-L-cysteine

L-Serine hydrochloride (10.0 g, 70.6 mmol) and 0.073 g (7.1 mmol) of triethylamine were dissolved in 100 ml of diethylene glycol dimethyl ether, and 16.8 g (141.2 mmol) of thionyl chloride was added dropwise at room temperature in a nitrogen gas atmosphere. After 2 hours of stirring at 60° C., 200 ml of water was added while maintaining the reaction system at 15° C. or below, and the resulting mixture was stirred at room temperature for 30 minutes. Further, 50 g of potassium carbonate was added to make the pH about 10 and, then, 17.9 g (141.2 mmol) of benzyl chloroformate was added dropwise. After overnight standing at room temperature, 10 g of potassium carbonate was again added to make the pH about 10 and, then, 10.7 g (97.1 mmol) of thiophenol was added dropwise at room temperature in a nitrogen gas atmosphere. After 2 hours of stirring at 60° C., the reaction mixture was cooled with ice and acidified with 50% sulfuric acid, and extracted with ethyl acetate. The solvent was distilled off and the residue was purified by column chromatography to give 8.7 g (26.2 mmol, 37%) of N-carbobenzyloxy-S-phenyl-L-cysteine. The product obtained had an optical purity of not less than 98% e.e. as determined by HPLC analysis in the same manner as in Example 13.

EXAMPLE 17

Production of N-carbobenzyloxy-S-phenyl-L-cysteine

β-Chloro-L-alanine hydrochloride (15.7 g, 98.1mmol) was added to 160 ml of water and dissolution was effected. The reactor inside was cooled to 0 to 5° C. and the pH was adjusted to 10 by dropwise addition of about 36 g of a 30% (by weight) aqueous solution of sodium hydroxide with vigorous stirring. While maintaining the inside temperature at 0 to 5° C., 20.5 g (120.0 mmol) of benzyl chloroformate was added dropwise over 1 hour with vigorous stirring and then stirring was continued for 4 hours, during which the pH of the reaction mixture was maintained at 9.5 to 10.5 by dropwise addition of about 16 g of a 30% (by weight) aqueous solution of sodium hydroxide. The reaction mixture obtained was assayed for N-carbobenzyloxy-β-chloro-L-alanine by HPLC and the yield thereof was found to be 25.1 g (97.5 mmol).

To the reaction mixture obtained was added dropwise 22.0 g (200.0 mmol) of thiophenol with vigorous stirring. During the dropping, the pH of the reaction mixture was maintained at 9.7to 10.3by dropwise addition of about 26g of a 30% (by weight) aqueous solution of sodium hydroxide. In a nitrogen atmosphere, the inside temperature was raised to 50° C. and the reaction was allowed to proceed for 3.5 hours, during which the pH of the reaction mixture was maintained at 9.7 to 10.3 by dropwise addition of about 1 g of a 30% (by weight) aqueous solution of sodium hydroxide. To the reaction mixture obtained was gradually added dropwise about 20 g of concentrated hydrochloric acid over 3 hours with vigorous stirring to thereby adjust the slurry pH to 3. The resulting precipitate crystals of N-carbobenzyloxy-S-phenyl-L-cysteine were filtered off under reduced pressure and sufficiently deprived of the liquid reaction medium by washing with two 100-ml portions of water, to give wet crystals of N-carbobenzyloxy-S-phenyl-L-cysteine [29.8 g (89.9 mmol) as pure N-carbobenzyloxy-S-phenyl-L-cysteine]. The optical purity of the N-carbobenzyloxy-S-phenyl-L-cysteine obtained was 99.9% e.e.

Comparative Example 4

Production of S-phenyl-L-cysteine

A 20% (by weight) aqueous solution of sodium carbonate e (2.23 g, 0.0042 mol) was added to 0.97 g (0.0088 mol) of thiophenol, and the mixture was stirred at room temperature for 0.5 hour. To this solution was added a solution composed of 1.08 g (0.0088 mol) of β-chloro-L-alanine and water, and the reaction was allowed to proceed for 5 hours, during which the pH of the reaction mixture was maintained at 8 to 10 while adding 5.14 g (0.0097 mol) of a 20% (by weight) aqueous solution of sodium carbonate. To the reaction mixture obtained were added 30 ml of toluene, 20 ml of water and about 3 g of concentrated hydrochloric acid in a nitrogen atmosphere to thereby adjust the pH to 0.5. The aqueous layer after separation from the organic layer was washed with two 30-ml portions of toluene to remove the remaining portion of thiophenol, to give 34.3 g of an aqueous solution of S-phenyl-L-cysteine.

HPLC analysis of the aqueous solution obtained revealed that the yield as pure S-phenyl-L-cysteine was 0.45 g (0.0023 mol, 26.0% yield). A marked extent of decomposition of β-chloro-L-alanine was observed.

INDUSTRIAL APPLICABILITY

The present invention, constituted as above, makes it possible to produce β-halogeno-α-aminocarboxylic acids, which are useful as starting materials for the production of medicinals, as well as optically active N-protected-S-phenylcysteines, which are useful as intermediates of medicinals, and intermediates thereof, in a simple, efficient and industrially advantageous manner and on a commercial scale.

What is claimed is:

1. A method of producing a β-halogeno-α-aminocarboxylic acid or a salt thereof
    which comprises halogenating the hydroxyl group of a β-hydroxy-α-aminocarboxylic acid, in which the basicity of the amino group in α-position is not masked by the presence of a substituent on said amino group, or a salt thereof with an acid by treating the same with a halogenating agent in a solvent containing an ether type solvent.
2. The method of producing according to claim 1,
    wherein the halogenating agent is a thionyl halide.
3. The method of producing according to claim 2,
    wherein the thionyl halide is thionyl chloride.
4. The method of producing according to claim 1,
    wherein the halogenating agent is used in an amount of 1 to 10 moles per mole of the β-hydroxy-α-aminocarboxylic acid.
5. The method of producing according to claim 1,
    wherein the ether type solvent is miscible with water.
6. The method of producing according to claim 5,
    wherein the water-miscible ether type solvent comprises at least one species selected from the group consisting of 1,2-dimethoxyethane, 1,4-dioxane, tetrahydrofuran, diethylene glycol dimethyl ether, triethylene glycol dimethyl ether, tetraethylene glycol dimethyl ether and polyethylene glycol dimethyl ether.
7. The method of producing according to claim 1,
    wherein the treatment with the halogenating agent is carried out in the presence of a hydrogen halide.
8. The method of producing according to claim 7,
    wherein the hydrogen halide is used in an amount exceeding 2.0 molar equivalents relative to the β-hydroxy-α-aminocarboxylic acid.
9. The method of producing according to claim 7,
    wherein the treatment with the halogenating agent is carried out in a state completely saturated or almost saturated with the hydrogen halide gas.
10. The method of producing according to claim 7,
    wherein the hydrogen halide is hydrogen chloride.
11. The method of producing according to claim 1,
    wherein the treatment with the chlorinating agent is carried out in the presence of an amine or a salt thereof.
12. The method of producing according to claim 11,
    wherein the amine is a tertiary amine.
13. The method of producing according to claim 1,
    wherein a coexisting hydrogen halide after treatment with the halogenating agent is converted to a salt form by means of a basic lithium compound, and dissolved in a medium composed of a water-miscible organic solvent and water while the β-halogeno-α-aminocarboxylic acid is caused to precipitate out in its free form.
14. The method of producing according to claim 13,
    wherein the water-miscible organic solvent comprises at least one species selected from the group consisting of 1,2-dimethoxyethane, 1,4-dioxane, tetrahydrofuran, diethylene glycol dimethyl ether, triethylene glycol dimethyl ether, tetraethylene glycol dimethyl ether, polyethylene glycol dimethyl ether, acetonitrile, methanol, ethanol, n-propanol, isopropanol, tert-butanol and acetone.
15. The method of producing according to claim 14,
    wherein the water-miscible organic solvent is acetone.
16. The method of producing according to claim 13,
    wherein the volume ratio of the water-miscible organic solvent to water is not less than 1.
17. The method of producing according to claim 13,
    wherein the final cooling temperature in the step of precipitation is not higher than 10° C.
18. The method of producing according to claim 1,
    wherein the low-boiling components occurring in the reaction mixture are reduced or eliminated beforehand after treatment with the halogenating agent but before precipitation of the desired product.
19. The method of producing according to claim 1,
    wherein, after treatment with the halogenating agent, the β-halogeno-α-aminocarboxylic acid in hydrohalogenic acid salt form that has precipitated from the reaction mixture as such or after concentration thereof is recovered.
20. The method of producing according to claim 1,
    wherein, after treatment with the halogenating agent, the reaction solvent is replaced with water to give an aqueous solution containing the β-halogeno-α-aminocarboxylic acid.
21. The method of producing according to claim 1,
    wherein the β-hydroxy-α-aminocarboxylic acid is serine, threonine, allothreonine or β-phenylserine.
22. The method of producing according to claim 21,
    wherein the β-hydroxy-α-aminocarboxylic acid is serine.
23. The method of producing according to claim 1,
    wherein the β-hydroxy-α-aminocarboxylic acid is optically active.
24. The method of producing according to claim 22,
    wherein the β-hydroxy-α-aminocarboxylic acid is L-serine.
25. A method of producing an optically active N-protected-β-chloroalanine of the general formula (2) or a salt thereof:

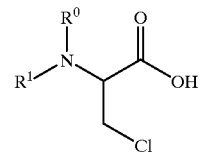

(2)

wherein $R^1$ represents an amino-protecting group and $R^0$ represents a hydrogen atom or, taken together with $R^1$, an amino-protecting group,
    which comprises preparing an optically active β-chloroalanine of the following formula (1) or a salt thereof:

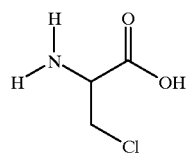

from an optically active serine or a salt thereof with an acid by the method of producing according to claim 1 and then treating the same with an amino-protecting agent.

26. The method of producing according to claim 25, wherein the halogenating agent is a thionyl halide.

27. The method of producing according to claim 25, wherein the amino-protecting agent is benzyl chloroformate and the optically active N-protected-β-chloroalanine is represented by the general formula (2) in which $R^0$ is a hydrogen atom and $R^1$ is a carbobenzyloxy group.

28. The method of producing according to claim 1, wherein the treatment with the halogenating agent is carried out at a temperature of 40–80° C.

* * * * *